United States Patent [19]

Schubart

[11] 4,240,983  
[45] Dec. 23, 1980

[54] MONOHALOGENATED KETONES

[75] Inventor: Rüdiger Schubart, Bergisch Gladbach, Fed. Rep. of Germany

[73] Assignee: Bayer Aktiengesellschaft, Leverkusen, Fed. Rep. of Germany

[21] Appl. No.: 81,224

[22] Filed: Oct. 2, 1979

Related U.S. Application Data

[63] Continuation of Ser. No. 891,563, Mar. 29, 1978, abandoned.

[30] Foreign Application Priority Data

Apr. 16, 1977 [DE] Fed. Rep. of Germany ....... 2716895

[51] Int. Cl.³ ............................................. C07C 45/63
[52] U.S. Cl. ................... 568/316; 549/64 D; 260/347.8; 260/326.5 R; 568/348; 568/393
[58] Field of Search ............... 260/593 H, 586 R, 592, 260/590 R; 549/64; 260/347.8, 326.5 R

[56] References Cited

U.S. PATENT DOCUMENTS

| | | | |
|---|---|---|---|
| 2,120,392 | 6/1938 | Calkins | 260/593 H |
| 2,168,260 | 8/1939 | Heisel et al. | 260/593 H |
| 2,235,562 | 3/1941 | Rahs | 260/593 H |
| 2,243,484 | 5/1941 | Morey | 260/593 H |
| 3,397,240 | 8/1968 | Kaufman et al. | 260/593 H |

FOREIGN PATENT DOCUMENTS

| | | | |
|---|---|---|---|
| 695048 | 7/1940 | Fed. Rep. of Germany | 260/593 H |
| 696772 | 8/1940 | Fed. Rep. of Germany | 260/593 H |

*Primary Examiner*—James H. Reamer  
*Attorney, Agent, or Firm*—Sprung, Felfe, Horn, Lynch & Kramer

[57] ABSTRACT

A process for the preparation of monohalogenated ketone is described wherein the ketone is vaporized in a collection vessel, and the vapors are caused to pass upwardly through a defined reaction zone into a condensation zone where they are condensed and caused to flow downwardly into the reaction zone. In the reaction zone their flow toward the collection zone is retarded, and while retarded, halogen is directed thereagainst. The halogenated ketone so formed is removed into the collection zone such as by directing condensed non-halogenated ketone thereagainst.

11 Claims, 3 Drawing Figures

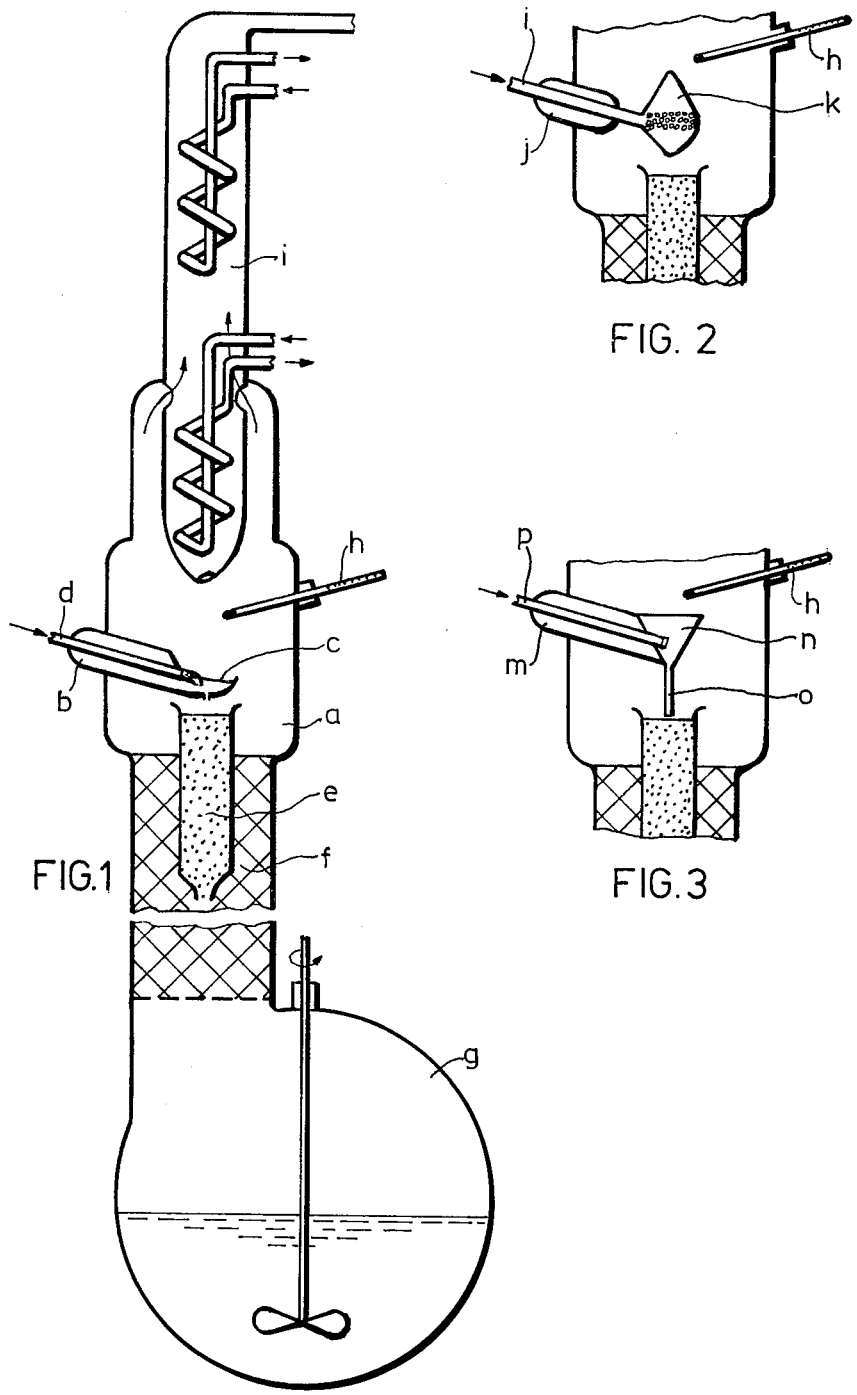

MONOHALOGENATED KETONES

This is a continuation, of application Ser. No. 891,563, filed Mar. 29, 1978 now abandoned.

The invention relates to a process for the selective preparation of monohalogenated ketones.

It is known to react gaseous ketones, which can be halogenated in the α-position, with gaseous chlorine which is blown in countercurrent to the carbon or the ketones (German Pat. Spec. No. 695,048 and German Pat. Spec. No. 696,772). Secondary reactions of the monochlorination product with further chlorine are decreased by this procedure.

According to the present invention there is provided a process for the preparation of a monohalogenoketone comprising vaporising a ketone in a vessel which is connected via a tube to a condenser, which condenser includes a reaction zone adjacent the tube and a collector located in the reaction zone above the open end of the tube, condensing the ketone vapour so that it drips onto the collector, introducing a halogen into the reaction zone, reacting the halogen with condensed ketone on the collector, and flushing the reaction product from the collector through the tube and back into the vessel, by means of further ketone dripping onto the collector.

The process according to the invention may be illustrated with the aid of the following equation:

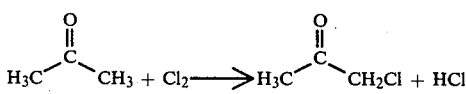

Ketones suitable for the process according to the invention can be, for example, compounds of the formula

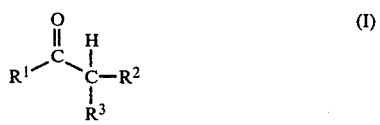

(I)

wherein

R$^1$ denotes an optionally substituted, straight-chain, branched or cyclic alkyl or alkylene radical or an optionally substituted aryl radical or, together with R$^2$ or R$^3$, a saturated or unsaturated hydrocarbon ring which optionally also contains, in the ring, nitrogen, oxygen or sulphur, and R$^2$ and R$^3$ are identical or different and denote hydrogen an optionally substituted, straight-chain, branched or cyclic alkyl or alkylene radical or an optionally substituted aryl radical or, together, form a saturated or unsaturated hydrocarbon ring which optionally also contains, in the ring, nitrogen, oxygen or sulphur. Ketones of the formula

(II)

wherein

R$^{1'}$ denotes an optionally substituted, straight-chain or branched C$_1$ to C$_{12}$ alkyl or C$_1$ to C$_{12}$ alkylene radical or an optionally substituted aryl radical or, together with R$^{2'}$ or R$^{3'}$ forms a saturated or unsaturated hydrocarbon ring or a nitrogen-, oxygen- or sulphur-contain hydrocarbon ring with 3 to 12 ring members. R$^{2'}$ and R$^{3'}$ are identical or different and denote hydrogen, an optionally substituted, straight-chain or branched C$_1$ to C$_{12}$ alkyl or C$_1$ to C$_{12}$ alkylene radical or an optionally substituted aryl radical or, together, form a saturated or unsaturated hydrocarbon ring or a nitrogen-, oxygen- or sulphur-containing hydrocarbon ring with 3 to 12 ring members, may be preferred.

Straight-chain or branched alkyl radicals (R$^1$, R$^2$ and R$^3$) which may be mentioned are hydrocarbon radicals with 1 to 18, preferably 1 to 12, carbon atoms, such as methyl, ethyl, propyl, isopropyl, butyl, isobutyl, pentyl, isopentyl, hexyl and isohexyl.

Cycloalkyl radicals (R$^1$, R$^2$ and R$^3$) which may be mentioned are cyclic hydrocarbon radicals with 4 to 12, preferably with 5 to 8, carbon atoms, such as cyclobutyl, cyclopentyl, cycloheptyl, cyclooctyl and cyclododecyl.

Straight-chain or branched alkenyl radicals (R$^1$, R$^2$ and R$^3$) which may be mentioned are unsaturated hydrocarbon radicals with 2 to 18, preferably 2 to 12, carbon atoms, such as ethenyl, propenyl, isopropenyl, butenyl, isobutenyl, pentenyl, isopentenyl, hexenyl and isohexenyl.

Cycloalkenyl radicals (R$^1$, R$^2$ and R$^3$) which may be mentioned are cyclic monounsaturated or polyunsaturated hydrocarbon radicals with 3 to 12, preferably 5 to 8, carbon atoms, such as cyclopentenyl, cyclohexenyl, cycloheptenyl and cyclooctenyl.

Aryl radicals (R$^1$, R$^2$ and R$^3$) which may be mentioned are aromatic hydrocarbon radicals with 6 to 10 carbon atoms, preferably phenyl, naphthyl and anthranyl.

Saturated hydrocarbon rings which are formed by linking the radicals R$^1$ and R$^2$ can have 3 to 12 ring members. Examples which may be mentioned are: cyclopropyl, cyclobutyl, cyclopentyl, cyclohexyl, cycloheptyl, cyclooctyl, cyclononyl, cycloundecyl and cyclododecyl.

Unsaturated hydrocarbon rings which are formed by linking the radicals R$^1$ and R$^2$ can have 3 to 12 ring members. Examples which may be mentioned are: cyclobutenyl, cyclopentenyl, cyclohexenyl, cycloheptenyl, cyclooctenyl, cyclodecenyl and cyclododecenyl, nitrogen-, oxygen- or sulphur-containing hydrocarbon rings which are formed by linking the radicals R$^1$ and R$^2$ can have 3 to 12 ring members. Examples which may be mentioned are: perhydrofuryl, perhydrothiophenyl, perhydro-N-methyl-pyrryl and perhydropyrryl.

Possible substituents of the radicals R$^1$, R$^2$ and R$^3$ are all the substituents which are not changed under the reaction conditions. Examples which may be mentioned are: lower alkyl radicals (C$_1$ to C$_4$), aryl, alkoxy (C$_1$ to C$_4$), aryloxy, alkylthio (C$_1$ to C$_4$), halogen, in particular chlorine and bromine, nitro and cyano.

The following ketones may be mentioned as examples of ketones for the process according to the invention: acetone, methyl ethyl ketone, diethyl ketone, methyl propyl ketone, ethyl propyl ketone, isopropyl propyl ketone, diisopropyl ketone, methyl tert.-butyl ketone, ethyl tert.-butyl ketone, propyl tert.-butyl ketone, butyl tert.-butyl ketone, methyl butyl ketone, ethyl butyl ketone, propyl butyl ketone, butyl butyl ketone, methyl isobutyl ketone, ethyl isobutyl ketone, propyl isobutyl ketone, butyl isobutyl ketone, methyl ethyl hexyl ketone, ethyl 2-ethylhexyl ketone, propyl 2-ethylhexyl ketone, butyl 2-ethylhexyl ketone, pentyl 2-ethylhexyl ketone, hexyl 2-ethylhexyl ketone, heptyl 2-ethylhexyl ketone, octyl 2-ethylhexyl ketone, decyl 2-ethylhexyl ketone, di-decyl ketone, methyl cyclohexyl ketone, ethyl cyclohexyl ketone, propyl cyclohexyl ketone, butyl cyclohexyl ketone, cyclohexanone, methylcyclohexanone, methyl cyclohexenyl ketone, methyl methylcyclohexyl ketone, methyl methylcyclohexenyl ketone, methyl phenyl ketone, ethyl phenyl ketone and propyl phenyl ketone, halogens for the process according to the invention can be fluorine, chlorine, bromine and iodine, preferably chlorine and bromine.

The process according to the invention can be carried out under reduced, normal or elevated pressure, preferably under normal pressure.

Anhydrous ketones can be used for the process according to the invention. Anhydrous ketones can be obtained, for example, by the incipient distillation of industrial ketones.

In a preferred embodiment of the process according to the invention, the reaction is carried out with water-containing ketones. In general, ketones which contain up to 20% by weight, preferably from 0.01 to 5% by weight, of water can be used.

In a further preferred embodiment of the process according to the invention, the reaction is carried out with the exclusion of light. The reaction temperature in the reactor can be $-20°$ to $120°$ C., but preferably $50°$ to $90°$ C. In the process according to the invention, the halogen is introduced into the reaction space in the gaseous state. The halogen can be employed without further diluents. However, it is also possible to dilute the gaseous halogen with inert gases, such as nitrogen or argon. The proportion of diluent can then be up to 90%, preferably up to 30–50%, of the gas employed.

Examples of possible devices which, in the process according to the invention, are let into the reaction space are constrictions of the reaction space which cause the ketone and the halogen to come into contact for a short time. The time should be calculated that the desired reaction proceeds to completion and, because of the very low residence time of all the reactants with one another, secondary reactions are almost impossible and thus virtually no by-products are obtained.

A constriction of the reaction space can be, for example, in the form of a device which is let into the reaction space and has, on the part located in the reaction space, a depression into which the gaseous halogen is fed, through a feed line, and is then reacted. In addition, it can be in the form of a hollow cone with a porous annular zone through which the gaseous halogen is fed into the thin liquid film running over the cone and is reacted directly.

It is also possible for the constriction to be in the form of a narrowing of the reaction space to give a tube, the upper part of which is in the form of a funnel and contains the gas inlet through which the gaseous halogen is directly passed, by means of a tube which is appropriately provided with a frit, into the hot liquid ketone, which has collected in the funnel.

The reflux ratio of gaseous halogen/liquid ketone for the process according to the invention is regulated so that less than the molar amount of halogen is present and it is used up by the reaction completely, immediately after emerging through the gas inlet. In general, the process according to the invention is carried out with a reflux ratio of 1 to 50 mols, preferably of 5 to 20 mols, of ketone per mol of halogen.

The choice of the most favourable constriction of the reaction space depends on the required contact time of the reactants. If the contact time is very short, a device let into the reaction space is preferred which is in the form of a cone. For longer reaction times it can be advantageous to use devices in which the part let into the reaction space is in the form of a depression.

The separation of the reaction mixture from the rising vapour of the ketone by means of a tube let into the column is a further characteristic of the process according to the invention. Examples of columns which may be mentioned are Vigreux columns, packed columns and bubble tray columns. In general, the tube let into the column can be packed with the same material as the surrounding column.

BRIEF DESCRIPTION OF DRAWING

An embodiment of the process according to the invention may be illustrated with the aid of FIGS. 1, 2 and 3, of the accompanying drawings, which represent possible apparatuses for the process.

A liquid ketone, optionally in the presence of water, is heated to the boil in a flask (g). The ketone, in the form of a vapour, rises through the column (f) and the reaction space (a) to the condenser (i) and is condensed there. In the case of FIG. 1, the condensate of the ketone runs onto the concave depression (c) of the device (b) let into the reaction space. In the case of Diagram 2, the ketone drips onto the tip of the cone (k) of the device (j) let into the reaction space. In the case Diagram 3, the ketone runs into the funnel (n), which is in the form of a tube (o) at the lower end, of the device (m) let into the reaction space.

The halogen, which can optionally be diluted with an inert gas, such as nitrogen or argon, is introduced through the gas inlet (d, 1 or p) of the devices (b, j or m) let into the reaction space and reacts with the ketone in the depression (c) or on the cone (k) or in the tube (o).

The monohalogenoketone formed is flushed out of the reaction space (a) by further ketone subsequently running from the condenser (i).

The mixture which runs off, which essentially consists of the monohalogenoketone formed and unreacted ketone, flows through the tube (e) let into the column (f) and is thus, separated from the rising vapour of the ketone, passed downwards. The mixture then flows further into the flask (g), from which the ketone is again vaporised. Since the monohalogenoketone as a rule has a higher boiling point than the ketone it remains in the flask and can be isolated in the customary manner, for example by distillation, after the reaction has ended.

The process according to the invention can also be carried out continuously, the starting materials being fed into the upper part of the apparatus and the end product being removed from the vaporiser.

Virtually all the customary materials, such as glass, quartz, Teflon and steel, can be used for the manufacture of the apparatus for the process according to the invention.

The process according to the invention can be carried out under reduced, normal or elevated pressure. By changing the pressure it is easily possible to employ a component in the most advantageous state of aggregation.

$\alpha$-Monohalogenoketones of the formula

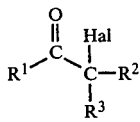

wherein

R[1], R[2] and R[3] have the meaning indicated above and

Hal represents fluorine, chlorine, bromine or iodine, can be prepared by the process according to the invention.

α-Monohalogenoketones of the formula

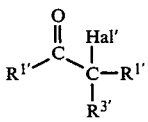

wherein

R[1'], R[2'] and R[3'] have the meaning indicated above and

Hal' represents chlorine or bromine, can preferentially be prepared by the process according to the invention.

The following α-monohalogenoketones may be mentioned as examples: 1-chloropropan-2-one, 1-chlorobutan-2-one, 3-chlorobutan-2-one, 1-chloro-3-methylbutan-2-one, 3-chloro-3-methyl-butan-2-one, 1-chloropentan-2-one, 3-chloropentan-2-one, 2-chloropentan-3-one, 1-chloro-3,3-dimethylbutan-2-one, 2-chloro-4-methylpentan-3-one, 1-chloro-3-methylpentan-2-one, 1-chloro-4-methylpentan-2-one, 3-chloro-3-methylpentan-2-one, 3-chloro-4-methylpentan-2-one, 2-chloro-4-ethylpentan-3-one, 1-chloro-3-cyclohexyl-butan-2-one, 1-chloro-4-cyclohexyl-butan-2-one, 3-chloro-4-cyclohexyl-butan-2-one, 1-chloro-3-ethylpentan-2-one, 1-chloro-4-ethylpentan-2-one, 3-chloro-3-ethylpentan-2-one, 3-chloro-4-ethylpentan-2-one, 1-chloro-3-isopropyl-pentan-2-one, 1-chloro-4-isopropyl-pentan-2-one, 1-chloro-4,4-dimethylpentan-2-one, 1-chloro-4,4-diethylpentan-2-one, 1-bromopropan-2-one, 1-bromobutan-2-one, 3-bromobutan-2-one, 1-bromo-3-methylbutan-2-one, 3-bromo-3-methylbutan-2-one, 1-bromopentan-2-one, 3-bromopentan-2-one, 2-bromopentan-3-one, 1-bromo-3,3-dimethylbutan-2-one, 2-bromo-4-methylpentan-3-one, 1-bromo-3-methylpentan-2-one, 1-bromo-4-methylpentan-2-one, 3-bromo-3-methylpentan-2-one, 3-bromo-4-methylpentan-2-one, 2-bromo-4-ethylpentan-3-one, 1-bromo-3-cyclohexylbutan-2-one, 1-bromo-4-cyclohexylbutan-2-one, 3-bromo-4-cyclohexylbutan-2-one, 1-bromo-ethylpentan-2-one, 1-bromo-4-ethylpentan-2-one, 3-bromo-3-ethylpentan-2-one, 3-bromo-4-ethylpentan-2-one, 1-bromo-3-isopropyl-pentan-2-one, 1-bromo-4-isopropyl-pentan-2-one, 1-bromo-4,4-dimethylpentan-2-one, 1-bromo-4,4-diethylpentan-2-one, 1-bromo-4-methyl-4-ethylpentan-2-one, 1-iodopropan-2-one, 1-iodobutan-2-one, 3-iodobutanon, 1-iodo-3-methylbutan-2-one, 3-iodo-3-methylbutan-2-one, 1-iodopentan-2-one, 3-iodopentan-2-one, 2-iodopentan-3-one, 1-iodo-3,3-dimethylbutan-2-one, 2-iodo-4-methylpentan-3-one, 1-iodo-3-methylpentan-2-one, 1-iodo-4-methylpentan-2-one, 3-iodo-3-methylpentan-2-one, 3-iodo-4-methylpentan-2-one, 2-iodo-4-ethylpentan-3-one, 1-iodo-3-cyclohexylbutan-2-one, 1-iodo-4-cyclohexylbutan-2-one, 3-iodo-4-cyclohexylbutan-2-one, 1-iodo-3-ethylpentan-2-one, 1-iodo-4-ethylpentan-2-one, 3-iodo-3-ethylpentan-2-one, 3-iodo-4-ethylpentan-2-one, 1-iodo-3-isopropylpentan-2-one, 1-iodo-4-isopropylpentan-2-one, 1-iodo-4,4-dimethylpentan-2-one, 1-iodo-4,4-diethylpentan-2-one, 1-bromo-4-methyl-4-ethylpentan-2-one, 1-chlorohexan-2-one, 3-chlorohexan-2-one, 2-chlorohexan-3-one, 4-chlorohexan-3-one, 1-chloro-3-methylhexan-2-one, 1-chloro-4-methylhexan-2-one, 1-chloro-5-methylhexan-2-one, 3-chloro-3-methylhexan-3-one, 3-chloro-4-methylhexan-2-one, 3-chloro-5-methylhexan-2-one, 1-chloro-3-ethylhexan-2-one, 1-chloro-4-ethylhexan-2-one, 1-chloro-3-isopropyl-hexan-2-one, 1-chloro-4-isopropylhexan-2-one, 2-chloro-4-methylhexan-3-one, 2-chloro-5-methylhexan-3-one, 4-chloro-4-methylhexan-3-one, 4-chloro-5-methylhexan-3-one, 2-chloro-4-ethylhexan-3-one, 2-chloro-4,4-dimethylhexan-3-one, 2-chloro-4,4-diethylhexan-3-one, 1-chloro-3-cyclohexylhexan-2-one, 1-chloro-4-cyclohexylhexan-2-one, 2-chloro-4-cyclohexyl-hexan-3-one, 2-chloro-5-cyclohexyl-hexan-3-one, chloromethyl cyclohexyl ketone, chloromethyl cyclohexenyl ketone, chloromethyl methylcyclohexyl ketone, 1-chloroheptan-2-one, 2-chloroheptan-3-one, 3-chloroheptan-2-one, 4-chloroheptan-3-one, 3-chloroheptan-4-one, 1-chloro-3-methylheptan-2-one, 1-chloro-4-methylheptan-2-one, 1-chloro-5-methylheptan-2-one, 1-chloro-6-methylheptan-2-one, 3-chloro-3-methylheptan-2-one, 2-chloro-4-methylheptan-3-one, 2-chloro-5-methylheptan-3-one, 2-chloro-6-methylheptan-3-one, 4-chloro-5-methylheptan-3-one, 1-chloro-3-isopropyl-heptan-2-one, 3-chloro-4-isopropyl-heptan-2-one, 1-chloro-3-ethyl-heptan-2-one, 2-chloro-4-ethyl-heptan-3-one, 2-chloro-5-ethylheptan-3-one, 1-chloro-3-ethylheptan-2-one, 1-chloro-4-ethylheptan-2-one, 1-chloro-5-ethylheptan-2-one, 3-chloro-4-ethylheptan-2-one, 3-chloro-5-ethylheptan-2-one, chlorocyclohexanone, chloromethylcyclohexanone, chloro-ethylcyclohexanone, chloro-isopropylcyclohexanone, 1-chlorooctan-2-one, 3-chlorooctan-2-one, 1-chlorononan-2-one, 3-chlorononan-2-one, 2-chlorononan-3-one, chlorocyclooctanone, chlorocyclononanone, chlorocyclodecanone, chlorocycloundecanone, chlorocyclododecanone, 1-chlorodecan-2-one, 3-chlorodecan-2-one, 1-chloroundecan-2-one, 3-chloroundecan-2-one, 1-chlorododecan-2-one, 3-chlorododecan-2-one, 2-chlorododecan-3-one, 4-chlorododecan-3-one, 1-chloro-tridecanan-2-one, 3-chlorotridecanan-2-one, 1-chloro-tetradecan-2-one, 3-chloro-tetradecan-2-one, 1-chloro-pentadecan-2-one, 3-chloro-pentadecan-2-one, 1-chloro-hexadecan-2-one, 3-chlorohexadecan-2-one, 1-chloro-heptadecan-2-one, 3-chloro-heptadecan-2-one, 1-chlorooctadecan-2-one and 3-chlorooctadecan-2-one.

α-Monohalogenoketones can be prepared in high yields and with high purity by the process according to the invention.

The α-monohalogenoketones which can be prepared by the process according to the invention can be employed as intermediate products for the preparation of plant protection agents or as vulcanisation accelerators.

EXAMPLES

A Reaction apparatus

The reaction apparatus represented in Diagram 1 is used in the examples which follow.

The apparatus consists of a vaporising vessel (g) which contains the ketone and optionally water. A column (f) filled with packing, into which an empty tube (e) which narrows towards the bottom is let, is mounted on the vaporising vessel (g). Above the column (f) is the reaction space (a) into which a device (b) is let, of which the part located in the reaction space is in the form of a depression (c).

The halogen is fed to the depression (c) from outside through the inlet (d) into the device (b).

In addition, the thermometer (h) is let into the reaction space (a) in order to monitor the reaction temperature.

The condenser (i) is arranged above the reaction space such that the liquid component condensed here can drip into the depression (c).

B Reaction of ketones with halogens in the reaction apparatus according to A

The reaction may be illustrated by the following examples:

258 g of diethyl ketone were reacted with a chlorine/nitrogen mixture (about 1:1) at 75°–82° C. (reaction temperature) in the presence of 6 g of water in a completely darkened apparatus. At a chlorination conversion of 88%, the chloride mixture contained 91.5% of 2-chloropentan-3-one. The mixture was fractionated: boiling point 135°–136° D; $n_D^{20}$ 1.484. Quantitative conversion is obtained with continuous chlorination. For this, chlorine and pentanone are fed into the apparatus at the top and the chlorination product is continuously removed from the vaporiser. The hydrochloric acid formed escapes at the head of the apparatus. The Examples 2 to 9 listed in the table which follows are carried out analogously to Example 1.

EXAMPLES 2 to 9

| Example | Ketone | Halogen | Monohalogenated ketone | Degree of conversion |
|---|---|---|---|---|
| 2 | acetone | chlorine | 98% of 1-chloropropan-2-one | 96% |
| 3 | 2-butanone | chlorine | 96.3% (1-chlorobutan-2-one and 3-chlorobutan-2-one) | 87% |
| 4 | 3-methylbutan-2-one | chlorine | 92.2% (1-chloro-3-methyl-butan-2-one and 3-chloro-3-methylbutan-2-one) | 91% |
| 5 | 2-pentanone | chlorine | 94% (1-chloropentan-2-one and 3-chloropentan-2-one) | 97% |
| 6 | 4-methylpentan-2-one | chlorine | 89.5% (1-chloro-4-methylpentanone and 3-chloro-4-methylpentanone) | 85% |
| 7 | pinacoline | chlorine | 94% of 1-chloropinacoline | 80% |
| 8 | pinacoline | bromine | 98% of 1-bromopinacoline | 76% |

What is claimed is:

1. In a process for the preparation of a monohalogenoketone by contacting a ketone with a halogen, the improvement which comprises vaporizing said ketone in a vessel and causing the vapors thereof to pass upwardly through a defined reaction zone into a condensation zone, condensing said ketone vapors in said condensation zone and causing liquid ketone in said condensation zone to drip downwardly into a collection zone, collecting said condensed liquid ketone in said collection zone, directing halogen against the liquid ketone while in said collection zone while in the presence of water and with the exclusion of light and passing the ketone after contact with said halogen in the presence of water and with the exclusion of light into said vessel by directing condensed non-halogenated thereagainst, the reaction of said halogen with said ketone being conducted at a temperature of −20° to 120° C. employing a mol ratio of ketone to halogen of 1 to 50:1.

2. A process according to claim 1 wherein the condensed ketone is collected in a concave depression.

3. A process according to claim 1 wherein the condensed ketone is collected on the internal walls of a funnel.

4. A process according to claim 1 wherein the condensed ketone is collected on the surface of an upwardly directed cone.

5. A process according to claim 1 wherein the halogenated ketone is flushed from said defined reaction zone by said non-halogenated ketone into a tube which feeds said vessel whereby the downwardly falling halogenated ketone is in out-of-contact relationship with rising vaporized ketone from said vessel.

6. A process according to claim 1 wherein 1 to 50 mols of ketone are employed per mol of halogen.

7. A process according to claim 1 wherein the reaction is carried out in the presence of 0.1 to 20% by weight of water per part of ketone.

8. A process according to claim 1 wherein the ketone has the formula

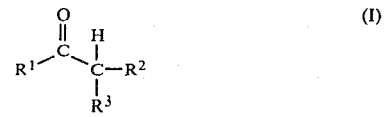

wherein
R¹ denotes an optionally substituted, straight-chain, branched or cyclic alkyl or alkylene radical or an optionally substituted aryl radical or, together with R² and R³, a saturated or unsaturated hydrocarbon ring which optionally also contains, in the ring, nitrogen, oxygen or sulphur, and
R² and R³ are identical or different and denote hydrogen, an optionally substituted, straight-chain, branched or cyclic alkyl or alkylene radical or an optionally substituted aryl radical or, together, form a saturated or unsaturated hydrocarbon ring which optionally also contains, in the ring, nitrogen, oxygen or sulphur.

9. A process according to claim 1 wherein the ketone has the formula

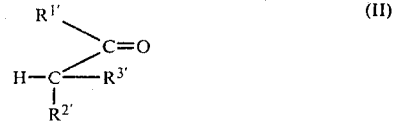

wherein
R¹' denotes an optionally substituted, straight-chain or branched $C_1$ to $C_{12}$ alkyl or $C_1$ to $C_{12}$ alkylene radical or an optionally substituted aryl radical or, together with R²' or R³' forms a saturated or unsaturated hydrocarbon ring of a nitrogen-, oxygen- or sulphur-containing hydrocarbon ring with 3 to 12 ring members, and
R²' and R³' are identical or different and denote hydrogen, an optionally substituted, straight-chain or branched $C_1$ to $C_{12}$ alkyl or $C_1$ to $C_{12}$ alkylene radical or an optionally substituted aryl radical or, together, form a saturated or unsaturated hydrocarbon ring or a nitrogen-, oxygen- or sulphur-containing hydrocarbon ring with 3 to 12 ring members.

10. A process according to claim 1 wherein said halogen is directed against said liquid ketone in concurrent flow.

11. A process according to claim 10 wherein said ketone is selected from the group consisting of acetone, methyl ethyl ketone, diethyl ketone, methyl propyl ketone, ethyl propyl ketone, isopropyl propyl ketone, diisopropyl ketone, methyl tert.-butyl ketone, ethyl tert.-butyl ketone, propyl tert.-butyl ketone, butyl tert.-butyl ketone, methyl butyl ketone, ethyl butyl ketone, propyl butyl ketone, butyl butyl ketone, methyl isobutyl ketone, ethyl isobutyl ketone, propyl isobutyl ketone, butyl isobutyl ketone, methyl ethyl hexyl ketone, ethyl 2-ethylhexyl ketone, propyl 2-ethylhexyl ketone, butyl 2-ethylhexyl ketone, pentyl 2-ethylhexyl ketone, hexyl 2-ethylhexyl ketone, heptyl 2-ethylhexyl ketone, octyl 2-ethylhexyl ketone, decyl 2-ethylhexyl ketone, didecyl ketone, methyl cyclohexyl ketone, ethyl cyclohexyl ketone, propyl cyclohexyl ketone, butyl cyclohexyl ketone, cyclohexanone, methycyclohexanone, methyl cyclohexenyl ketone, methyl methylcyclohexyl ketone, methyl methylcyclohexenyl ketone, methyl phenyl ketone, ethyl phenyl ketone and propyl phenyl ketone.

* * * * *

UNITED STATES PATENT AND TRADEMARK OFFICE
CERTIFICATE OF CORRECTION

PATENT NO. : 4,240,983
DATED : December 23, 1980
INVENTOR(S) : Rüdiger Schubart

It is certified that error appears in the above—identified patent and that said Letters Patent is hereby corrected as shown below:

Column 6, line 8, "-3-one" should be -- -2-one --

*Signed and Sealed this*

*Twenty-fourth* Day of *March 1981*

[SEAL]

Attest:

*Attesting Officer*

RENE D. TEGTMEYER

*Acting Commissioner of Patents and Trademarks*